United States Patent [19]

Geddes et al.

[11] Patent Number: 5,092,339
[45] Date of Patent: Mar. 3, 1992

[54] METHOD AND APPARATUS FOR ELECTRICALLY COMPENSATED MEASUREMENT OF CARDIAC OUTPUT

[76] Inventors: Leslie A. Geddes, 400 N. River Rd.; Joe D. Bourland, 606 Wilshire; William D. Voorhees, III, 5010 Swisher Rd.; Neal E. Fearnot, 3051 Hamilton St.; Anthony C. Raghep, 28-11 Tower Dr., all of West Lafayette, Ind. 47907; Frederick J. Shipko, P.O. Box 24, Spring Church, Pa. 15686

[21] Appl. No.: 557,135

[22] Filed: Jul. 23, 1990

[51] Int. Cl.$^5$ ............................................. A61B 5/02
[52] U.S. Cl. ................................... 128/692; 128/734; 128/673; 128/693
[58] Field of Search ................ 128/692, 693, 713, 695, 128/734, 673

[56] References Cited

U.S. PATENT DOCUMENTS

| | | | |
|---|---|---|---|
| 3,896,373 | 7/1975 | Zelby | 128/692 |
| 4,105,022 | 8/1978 | Antoshkiw et al. | 128/671 |
| 4,380,237 | 4/1983 | Newbower | 128/693 |
| 4,572,206 | 2/1986 | Geddes et al. | 128/698 |
| 4,573,473 | 3/1986 | Hess | 128/696 |
| 4,676,252 | 6/1987 | Trautman et al. | 128/692 |
| 4,785,823 | 11/1988 | Eggers et al. | 128/692 |
| 4,898,176 | 2/1990 | Petre | 128/713 |
| 4,899,759 | 2/1990 | Pederson et al. | 128/693 |

OTHER PUBLICATIONS

G. N. Stewart, "The Output of the Heart in Dogs," *Journal of Physiology* 57:27–50 (1921).

Newbower et al., "Sensor for Catheter-Based Measurements of Electrical Conductivity," *IEEE Transactions on Biomedical Engineering*, Feb. 1986, vol. BME-33, No. 2.

Geddes et al., "Electrical Calibration of the Saline-- Conductivity Method for Cardiac Output: A Preliminary Report," *Cardiovascular Research Center*, 10:91-106 (1972).

Geddes et al., "Cardiac output using an electrically calibrated flow-through Conductivity Cell," *Journal of Physiology*, 37:972-977 (1974).

Geddes et al., "The Rectification Properties of an Electrode-Electrolyte Interface Operated at High Sinusodial Current Density," *IEEE Transactions on Biomedical Engineering*, Sep. 1987, vol. BME-34, No. 9, 669-672.

Boheim et al., "Rate-Responsive Pacemaker with Intracardiac Volume Feedback Control," Pacer-Gram, Biotronik, Jul. 1988, vol. 5, No. 2.

"Blood Resistivity Measured with New BioMedical Device," *Extrapo the Purdue Engineering Alumni Magazine*, Spring 1984, vol. 11, No. 3.

van Oosterom et al., "Intramural resistivity of cardiac tissue," *Medical & Biological Engineering & Computing*, 1979, 17, 337-343.

(List continued on next page.)

[57] ABSTRACT

Cardiac output is measured using an injected substance (indicator) that changes the conducting property (electrical resistivity) of blood, provided the indicator has a different resistivity from that of blood. A new type of electrically compensated tetrapolar conductivity cell located at the distal end of an intravascular catheter is disclosed. The conductivity cell consists of four electrodes arranged across the end of a catheter at its tip. The outer electrodes used for current injection are enlarged to reduce the electrode-electrolyte interface impedance. Capacitance compensation of the cather/-tetrapolar conductivity cell provides reliable and repeatable blood resistivity measurements. The catheter further includes a calibration resistor thereby eliminating a calibration step previously necessary in using such a catheter for measuring cardiac output.

23 Claims, 5 Drawing Sheets

OTHER PUBLICATIONS

Constantinesco et al., "Intravascular mean blood velocity measurements using a crosscorrelation technique," *Medical & Biological Engineering & Computing*, 1980, 18, 439-446.

Grubbs et al., "Right-Side Cardiac Output Determined with a Newly Developed Catheter-Tip Resistivity Probe Using Saline Indicator," *Japanese Heart Journal*, Jan. 1984, vol. 25, No. 1, 105-111.

"Right Heart Output Using Sodium Chloride Indicator," *IEEE/NSF Symposium on Biosensors*, 1984, 20-23.

Geddes et al., *Principles of Applied Biomedical Instrumentation*, 2nd Edition (1975) pp. 308-3111, 328-329, 330-342, 372-373.

Geddes et al., *Cardiovascular Devices and Their Applications*, 1984, pp. 117-122.

Grubbs et al., "A New Technique for Obtaining Values of Cardiac Output in Rapid Succession," *IEEE Transactions on Biomedical Engineering*, Dec. 1982, vol. BME-2 No. 12, 769-772.

Geddes et al., *Electrodes and the Measurement of Bioelectric Events*, 1972, pp. 178-190.

Bourdillon et al., "Saline Conductivity Method for Measuring Cardiac Output Simplified", *Medical & Biological Engineering & Computing*, 1979, 17, 323-329.

*Primary Examiner*—Francis Jaworski
*Assistant Examiner*—George Manuel
*Attorney, Agent, or Firm*—Woodard, Emhardt, Naughton, Moriarty & McNett

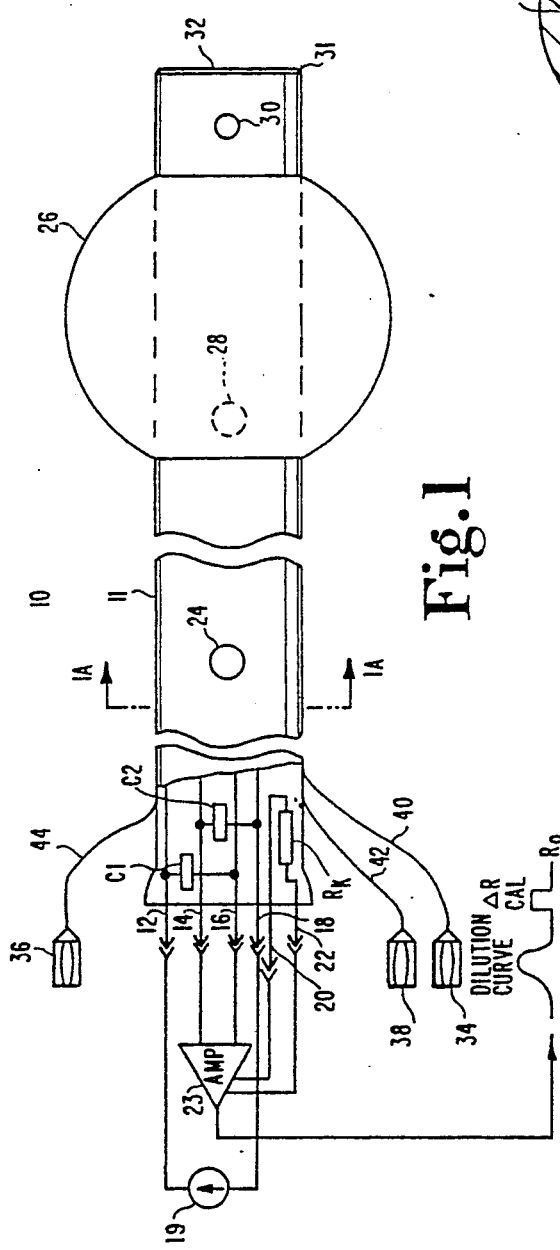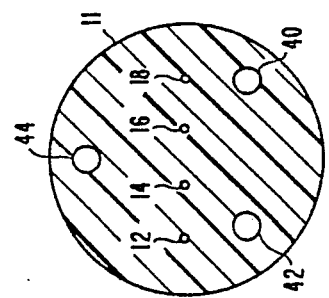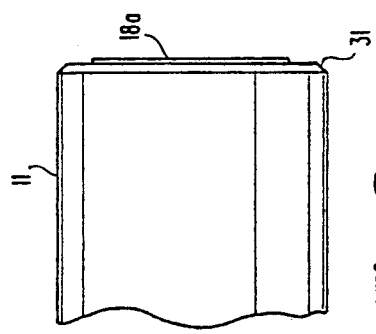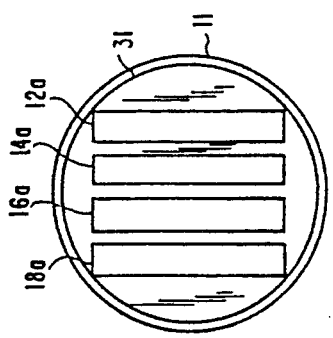

METHOD AND APPARATUS FOR ELECTRICALLY COMPENSATED MEASUREMENT OF CARDIAC OUTPUT

BACKGROUND OF THE INVENTION

This invention relates to a method and apparatus for measuring blood flow using an indicator such as a saline solution, and, more particularly, relates to such a method and apparatus using an improved conductivity cell positioned at the tip of a catheter.

As shown, for example, in U.S. Pat. No. 4,572,206 to Geddes et al., a tetrapolar conductivity cell mounted on the tip of a catheter can be used to determine cardiac output or volumetric blood flow. It has been found through the course of work in this area that the construction of the catheter conductivity cell plays a role in the accuracy and repeatability of such determinations. Cardiac output measurements taken with an individual catheter conductivity cell of the type described in the aforementioned Geddes et al. patent were found to vary over time in a controlled environment, and subsequent efforts to improve the repeatability resulted in identification of certain structural features as contributing to performance problems. Stray and distributed capacitance between the conductors along the length of the catheter, and positioning of the conductivity cell leads within the body of the catheter, were identified as sources of repeatability errors associated with the measurement of cardiac output using the dilute saline indicator technique. Additionally, the surface area of the conductivity cell electrodes in contact with the blood appeared to have some effect on performance and repeatability of the catheter conductivity cell.

Newbower and Troutman described a different type of conductivity cell for measuring cardiac output in "Sensor for Catheter-Based Measurement of Electrical Conductivity", *IEEE Transactions Biomedical Engineering* (1986), BME 33:182-188. The Newbower/Troutman device was patented in U.S. Pat. No. 4,380,237. Newbower and Troutman took a fundamentally different approach to that suggested in the aforementioned patent to Geddes et al., in that their conductivity cell is side-looking, i.e., its electrodes are arranged on the side of the catheter body rather than across the tip of the catheter. The Newbower/Troutman location for the conductivity cell runs the risk of producing large errors in resistivity measurement when the catheter comes close to the wall of a blood vessel, as frequently occurs. Moreover, the Newbower/Troutman design fails to deal with the electrical shunting effect due to the capacitance present between the four electrode wires within the catheter body. It is now believed that capacitance attributable to the four electrode wires within the catheter results in deviations in the conductivity cell constant from what would be theoretically calculated according to the geometry of the electrodes such that the Newbower/Troutman device would, like the aforementioned Geddes et al. device, exhibit less than optimal repeatability.

SUMMARY OF THE INVENTION

This invention provides an improved device and method for monitoring and measuring cardiac output. One embodiment of an apparatus according to the present invention enables measurement of cardiac output by determination of blood resistivity and its change by the injection of dilute saline. The apparatus comprises a conductivity cell having a plurality of electrodes, capacitance compensation means connected to the conductivity cell for neutralizing stray and distributed capacitances, and positioning means for placing the conductivity cell in the flow path of blood.

In another embodiment of the present invention, an indicator-dilution method for measuring cardiac output comprises the steps of placing a conductivity cell in the flow path of blood, compensating for stray and distributed capacitances of the conductivity cell, electrically calibrating the conductivity cell without withdrawing blood from the flow path, the calibrating being accomplished by utilizing the conductivity cell to generate an output signal indicative of baseline blood resistivity, injecting an indicator into the blood flow path and obtaining an output signal from the conductivity cell indicative of blood resistivity as altered by the indicator, and determining cardiac output from the output signal indicative of baseline blood resistivity and the output signal indicative of altered blood resistivity which describes an indicator-dilution curve.

It is therefore an object of this invention to provide an improved device and method for measuring cardiac output.

It is yet another object of this invention to provide a catheter-tipped conductivity cell with capacitance neutralization for the measurement of blood resistivity, thereby minimizing distributed capacitance effects on measurement accuracy.

It is an objective of one embodiment of the invention to locate a conductivity cell at the tip of a catheter with electrodes of maximum surface area to ensure a low impedance contact with the blood.

It is a further objective of one embodiment of the invention to use an electrical component incorporated into the catheter-tip conductivity cell to identify the particular conductivity cell constant of the catheter assembly.

Related objects and advantages of the present invention will be apparent from the following Description of the Preferred Embodiment.

BRIEF DESCRIPTION OF THE DRAWINGS

FIG. 1 is a front view illustrating the cardiac output monitor catheter assembly according to the present invention shown connected to an excitation source and an isolation amplifier.

FIG. 1A is a cross-sectional view of the catheter of FIG. 1 looking in the direction of the arrows labeled 1A.

FIG. 2 is an end view illustrating one arrangement for the electrodes at the distal end of the catheter of FIG. 1.

FIG. 3 is a magnified front view illustrating the distal end of the catheter of FIG. 1

DESCRIPTION OF THE PREFERRED EMBODIMENT

Figure 1B:
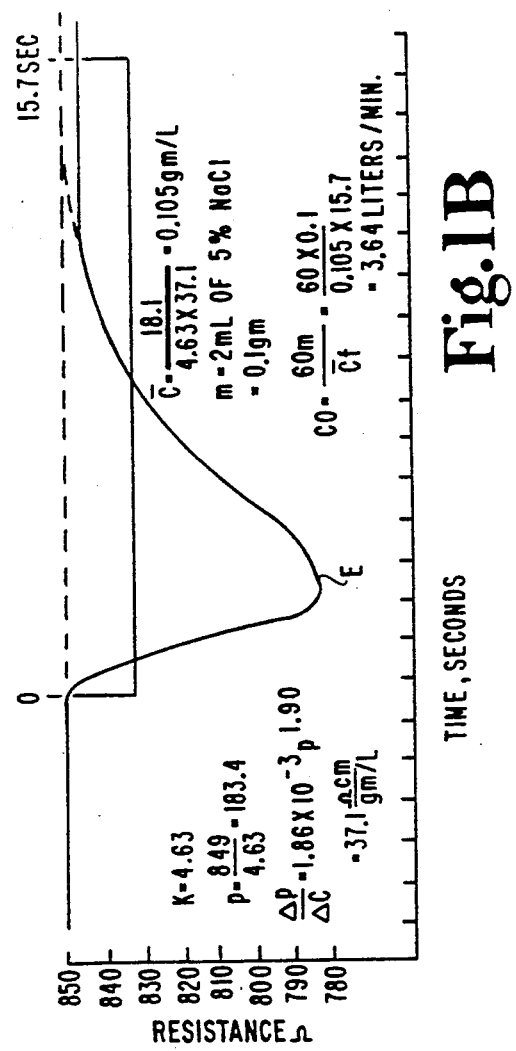
FIG. 1B is a typical dilution curve corrected for recirculation and a sample calculation of cardiac output using $\rho$ and $\Delta\rho/\Delta C$ with the conductivity cell having a constant K.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now to FIG. 1, an electrically compensated tetrapolar catheter-tip conductivity cell catheter 10 according to the present invention is shown. Conductors 12, 14, 16 and 18, preferably formed of stainless steel or other suitable metal, extend internally along the entire length of catheter 11 and emerge at the distal end 32 of catheter 11. The conductors 12, 14, 16 and 18 are formed or flattened to enlarge the surface area of each conductor at the distal end 32 to create an electrode having a surface area much larger than the cross-sectional area of the conductors. The flattened conductors or electrodes may be short metal sleeves placed over the conductors at the tip and flattened at the distal end 32 of catheter 10 and attached to the distal end 32 with epoxy 31 or an equivalent resin.

Figure 8:
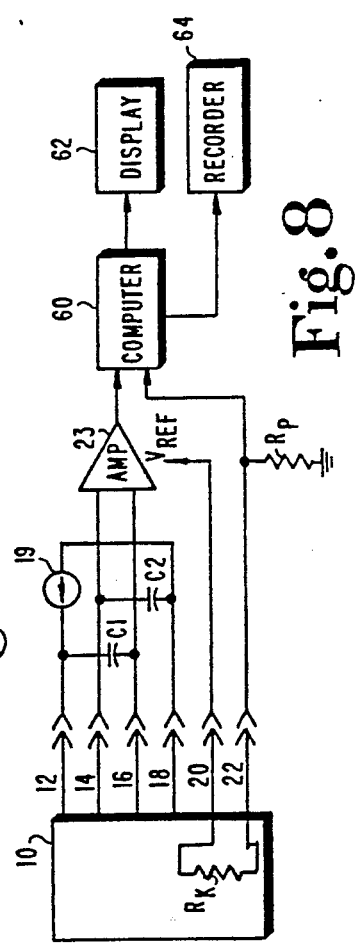
FIG. 8 is a block diagram schematic illustrating an alternate arrangement for connecting the catheter of FIG. 1 to measurement equipment.

Located internally within catheter body 11, capacitor C1 is connected to conductor 12 and conductor 16. Capacitor C2 is connected to conductor 14 and conductor 18. Capacitors C1 and C2 are located internally within the catheter body but may also be located in a cable connecting the catheter 11 to the measurement equipment as shown in FIG. 8. Conductors 20 and 22 extending from the catheter body 11 are connected to resistor $R_K$. Resistor $R_K$ is used to identify certain electrical characteristics of the catheter, more particularly the conductivity cell constant of the tetrapolar conductivity cell comprised of conductors 12, 14, 16, and 18 and the corresponding electrodes at end 32.

Balloon inflation fitting 36 is attached to one end of balloon inflation lumen 44. Balloon inflation lumen 44 extends within catheter body 11 and communicates with balloon inflation port 28. Pressurized air is supplied through lumen 44 to inflate the catheter balloon 26. The saline indicator inject fitting 34 is connected to one end of indicator injection lumen 40. The distal end of lumen 40 emerges at port 24, at a location upstream in the vascular system from the distal end 32 of the catheter. Pressure measurement fitting 38 is attached to and communicates with pressure measurement lumen 42. Pressure measurement lumen 42 extends through the catheter body 11 to the pressure measurement port 30 near the distal end 32 of the catheter 11. Pressure measurement port 30 may also be located at the distal end 32 of catheter body 11 or on the lateral surface of the catheter body 11 as shown.

Amplifier 23 is connected to conductors 14 and 16. Resistor $R_K$, also connected to amplifier 23, supplies a gain control resistance to amplifier 23. The gain factor effected by resistor $R_K$ compensates for the characteristics peculiar to each individual catheter and accompanying tetrapolar conductivity cell. The constant current source 19 supplies a constant alternating current signal to conductors 12 and 18. Amplifier 23 is a very high input impedance operational amplifier or op amp. Alternatively, it is contemplated that amplifier 23 can be an instrumentation amplifier, a commonly known isolated input op amp circuit having a high common mode rejection ratio and which produces a ground referenced output signal from isolated differential input signals. The output of amplifier 23, after demodulation, provides the dilution curve and calibration information for calibrating the measurement equipment to produce the resistivity curve shown in FIG. 1B.

Figure 1C:
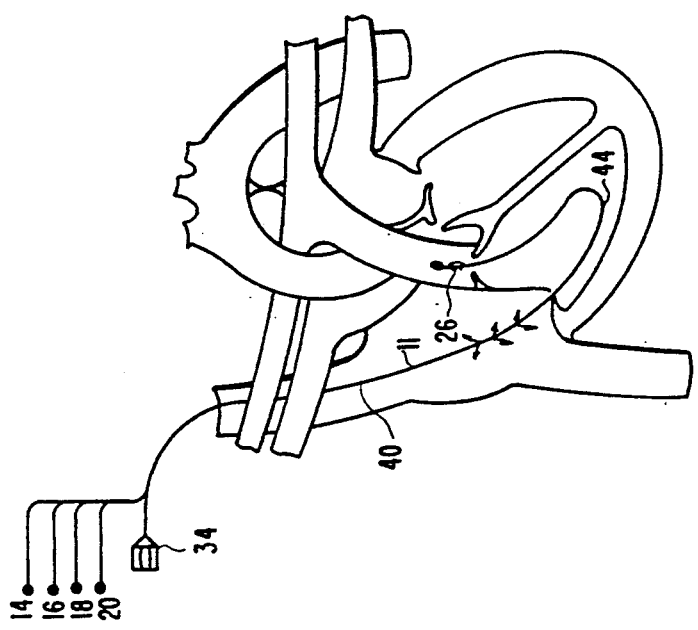
FIG. 1C is a partial perspective view illustrating one typical positioning of a tetrapolar conductivity cell at the tip of a catheter in the vascular system.

Use of the apparatus shown in FIG. 1 for recording conductivity in the pulmonary artery is shown schematically in FIG. 1C.

With respect to use as shown in FIG. 1C, only a single vessel, e.g. arm vein 65, need be used to insert the apparatus into the pulmonary artery. Catheter 10 preferably includes a balloon 26 for flow guidance, a balloon inflation lumen (generally indicated by the numeral 44) and a second lumen (generally indicated by the numeral 40) for injecting the indicator (by means of inject fitting 34) connected with an inlet port (not shown). In the preferred embodiment, a third lumen is also included for recording pressure, and as an aid for catheter placement. The identification of the location of the catheter tip can also be made by recording the electrocardiogram from the catheter electrode and an indifferent electrode placed at any convenient site on the subject. The electrodes 12, 14, 16, and 18 positioned at the tip of the catheter provide output signals which are coupled to the circuitry as shown in FIG. 1 or in FIG. 8. The output signal measured across electrodes 14 and 16 enables measurement of blood resistivity and inscribing a dilution curve in the same manner as described in the patent to Geddes et al., U.S. Pat. No. 4,572,206.

Referring now to FIG. 2, a view of the distal end 32 of the catheter 11 of FIG. 1 is shown. The four electrodes 12A, 14A, 16A and 18A are formed by flattening and bending the four conductors 12, 14, 16 and 18, respectively, which conductors are extruded integral with catheter body 11. The electrode surface areas can be made larger by placing short metal tubes over the electrode wires and flattening them. Stainless steel or other suitable material can be used for the conductors and the electrodes formed at the ends of the conductors. Epoxy 31 or another suitable resin is used to secure the conductors to the distal end 32 of catheter body 11. After the epoxy hardens, the electrodes are exposed by gentle rubbing with abrasive paper such as sandpaper. It is well known to those skilled in the art that the end over which the electrodes are folded could be wedge-shaped, hemispherical or any other geometrically conceivable form.

Referring now to FIG. 3, a more detailed side view of the distal end 32 is shown. In particular, the detail of the epoxy 31, and exposed electrode 18A is shown to reveal more particularly the construction of the catheter 10 according to the present invention. The electrodes are exposed by wet sanding to produce a uniformly clean and smooth surface. The epoxy rigidly fixes the electrodes in position.

Rigid fixation of the electrodes 12a, 14a, 16a, and 18a is important to prevent variations in the conductivity cell constant and thus allow use of a fixed calibration resistor. Without rigid fixation of the electrodes, bending, flexing and stretching of the catheter body 11 can result in movement of the electrodes with respect to one another, thereby changing the conductivity cell constant. Temperature change from room temperature to body temperature softens the plastic used to construct the catheter body 11 and thus has a marked effect on the mechanical characteristics of the catheter body 11. Hence, fixing the electrodes in position relative to one another at the tip of the catheter body 11 is important for the compensation scheme to improve stability of measurements made with the catheter 10 in practical use.

Referring now to FIG. 1A, a cross-section of the catheter body 11 at the location marked 1A of FIG. 1 is shown. The location of the stainless steel conductors 12, 14, 16 and 18 within the catheter 11 is indicated by FIG. 1A. Further, the pressure measurement lumen 42, balloon inflation lumen 44, and indicator injection lumen 40 are also shown. For ease of extrusion the conductors 12, 14, 16 and 18 all lie in a plane with equal spacing therebetween. Geometric symmetry in construction of the catheter aids in producing reliable and repeatable results.

Figure 4A:
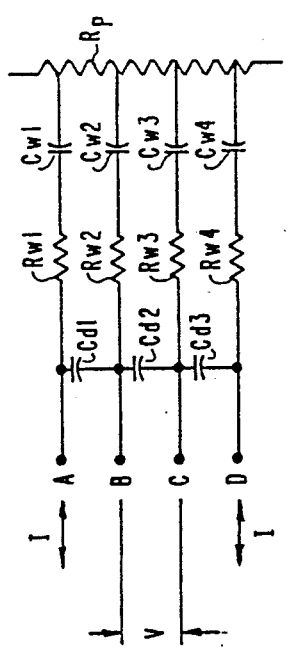
FIG. 4A is an electrical schematic diagram illustrating the prior art equivalent circuit for a tetrapolar conductivity cell cardiac output monitor catheter.

The equivalent circuit of a tetrapolar conductivity cell according to the Warburg model for an electrode-electrolyte interface is shown in FIG. 4A. The Warburg model of the electrode-electrolyte interface ($R_w C_w$) is illustrated. The equivalent circuit of each electrode-electrolyte interface is represented by resistors labeled $R_{wx}$ and $C_{wx}$, where "x" is a number 1 through 4, as shown in FIG. 4A. An AC signal is injected via electrodes "A" and "D" and the potential measured between electrodes "B" and "C" identifies the resistivity ($\rho$) of the blood. More specifically, the voltage across electrodes "B" and "C" divided by the injected current "I" is equal to the product of "k" and "$\rho$", where k is the conductivity cell constant, a quantity that depends on the spacing and location of the potential measuring electrodes "B" and "C". The use of a constant current source to feed the current electrodes "A" and "D", and a high input impedance device to measure the voltage across electrodes "B" and "C" eliminates any error in measurement due to the impedances constituted by the electrode-electrolyte interface ($R_{wx}$ and $C_{wx}$) impedance.

However, when a conductivity cell is incorporated into a catheter, the distributed capacitance $C_{d1}$, $C_{d2}$, and $C_{d3}$ between the conductors, as shown in FIG. 4A, results in an error in resistivity ($\rho$) measurement. As the capacitance of capacitors $C_{d1}$, $C_{d2}$, and $C_{d3}$ increases, a greater amount of the signal injected into conductors A & D is bypassed to conductors B and C via the distributed capacitance phenomenon.

Figure 6:
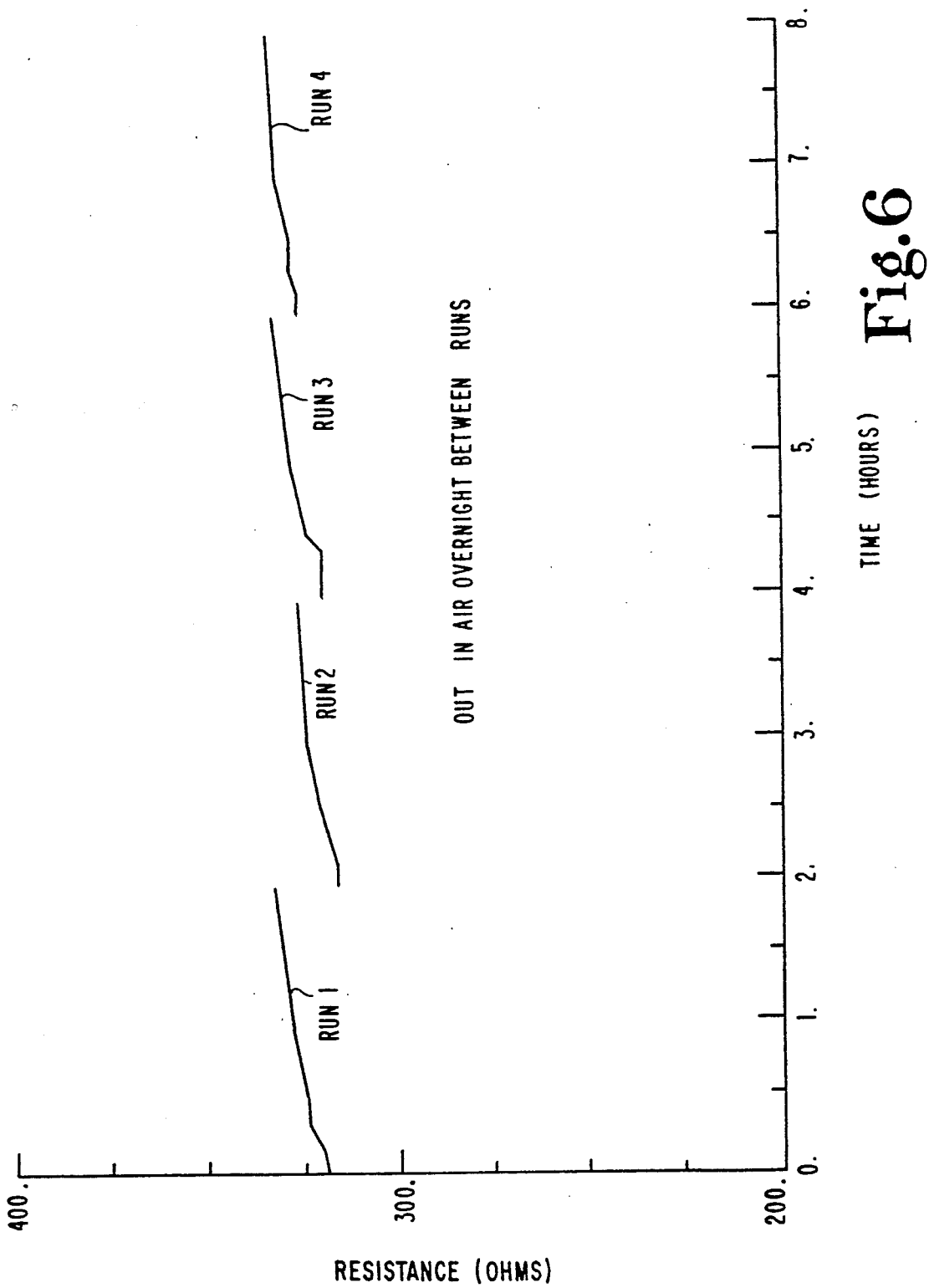
FIG. 6 is a graph illustrating the impedance drift of an uncompensated tetrapolar conductivity cell cardiac output monitor catheter.

A simple (uncompensated) catheter-tip conductivity cell can be unstable. To demonstrate this fact, a catheter tip conductivity cell was fabricated with 0.005 inch diameter stainless steel conductors in a 7 French (7F) catheter with the conductors arranged in parallel as shown in the Geddes et al. patent. The sensing tip of the catheter was placed into a saline solution and maintained at a constant temperature for 2 hours, after which the catheter conductivity cell was removed and allowed to stand overnight. Thereafter, the sensing tip was placed into the same saline solution as previously used. This procedure was repeated daily. A record of the resistance recorded for the catheter is shown in FIG. 6. Note that there is an upward drift to the measured resistivity by the catheter with each repeated trial in the above-described drift testing procedure.

The resistance drift is believed, in part, due to corrosion of electrodes 12 and 18 (the current-injecting electrodes). If operated at a high current density, rectification occurs and the edges of electrodes 12 and 18 that face each other become corroded. This effect depends primarily on the type of metal used to construct the electrodes, current density, and frequency of the current. Drift attributable to these sources can be minimized by selection of an appropriate current density for the frequency of the injected signal. According to an article by Geddes, et al., "The Rectification Properties of an Electrode-Electrolyte Interface Operated at High Sinusoidal Current Density," *IEEE Transactions on Biomedical Engineering*, Volume BNE-34, No. 9, September, 1987, the rectifying properties of a stainless steel/saline electrode-electrolyte interface vary with frequency, current density and electrode material. At each frequency tested with increasing current density, it was found that a threshold current density for current rectification existed. Additionally, the most sensitive indicator of approaching rectification was the increase in the (Warburg) capacitance of the electrode-electrolyte interface as current was increased to the interface. For the present invention, the preferred frequency is 10 kHz, and current level is 10 $\mu$A pk-pk, for a 7 French catheter with leads as described above, having 0.010 inch lead spacing and electrode surface areas of 0.0015 cm$^2$ for the current injection electrodes 12 and 18 and 0.0011 cm$^2$ for the voltage sensing electrodes 14 and 16. Gentle wet sanding of the electrodes produces a finish having more electrically stable characteristics.

Figure 4B:
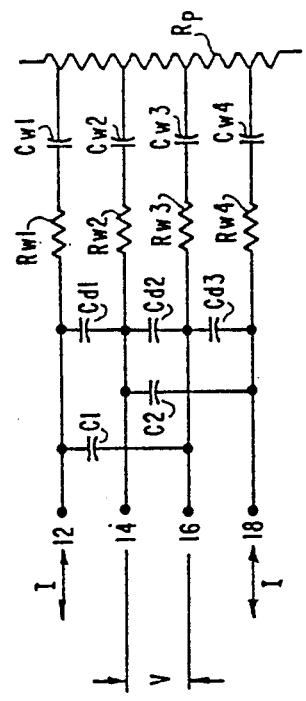
FIG. 4B is an electrical schematic diagram illustrating the equivalent circuit of the cardiac output monitor catheter of FIG. 1 with compensating capacitors C1, C2.

Referring now to FIG. 1, capacitive coupling between conductors 12 and 14 and conductors 16 and 18 feeds an unwanted signal into the voltage-measuring device connected to electrodes 14 and 16. The closer electrode 12 is to electrode 14, and the closer electrode 18 is to electrode 16, the greater the capacitive coupling between the conductors. With the four conductors constrained in a small-diameter catheter, the spacing of the conductors is severely limited. In addition, if the length of the catheter is increased, the capacitive coupling or distributed capacitance between the conductors increases. Therefore, in order to avoid error in measuring resistivity with the tetrapolar conductivity cell catheter, it is necessary to minimize the error due to capacitive coupling. By feeding a selected out-of-phase voltage to conductors 14 and 16 via capacitors C1 and C2, it is possible to cancel the capacitive error. For example, the stray capacitances $C_{d1-d3}$ of FIG. 4A are compensated or neutralized by applying out-of-phase signals via small neutralizing capacitors C1 and C2 as shown in FIG. 4B. FIG. 4B illustrates the addition of capacitors C1 and C2 to the equivalent circuit of the tetrapolar cardiac output monitor catheter of FIG. 4A. Because of the fact that the impedances of the (Warburg) electrode-electrolyte interface $R_w C_w$ are in the current injecting and measuring circuits, the value of the compensating capacitor is selected on the basis of the size and spacing of the four conductors within the catheter body 11 of FIG. 1.

The neutralizing capacitors may alternatively be located in the electronic measurement device used with the catheter conductivity cell, or in the connector of the catheter-conductivity cell. If, however, an extension cable is used, the neutralizing capacitors can be installed in the connectors at either end of the extension cable.

Figure 7:
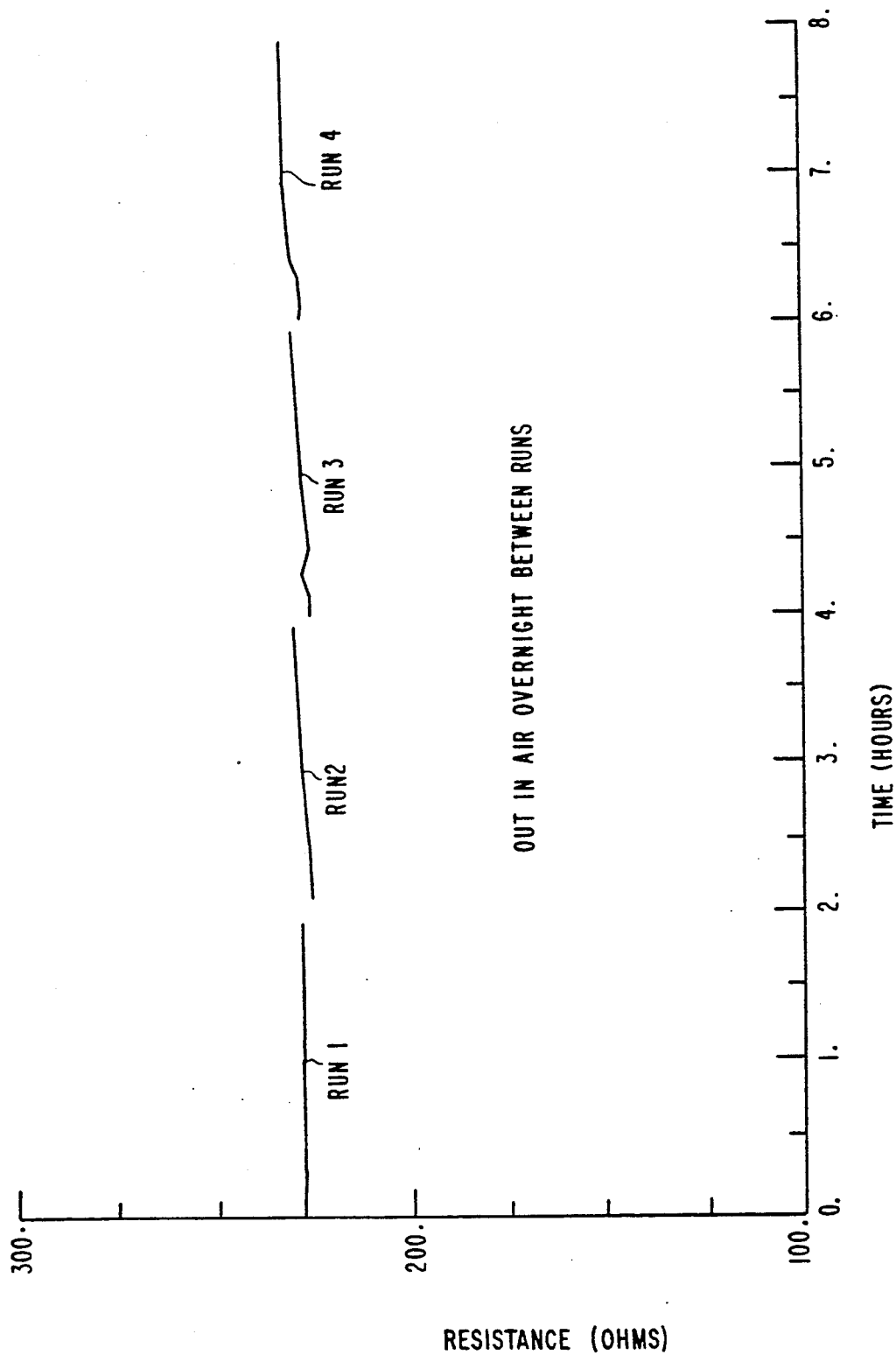
FIG. 7 is a graph illustrating the impedance drift of a capacitance compensated tetrapolar conductivity cell cardiac output monitor catheter.

To eliminate the drift due to stray capacitance, capacitive neutralization was applied in the manner shown in FIG. 4B. A neutralizing capacitor C1 is connected between conductors 12 and 16, and a second neutralizing capacitor C2 is connected between conductors 14 and 18. The stability test described above was repeated with a value of 47 pF for C1 and C2, and the result is shown in FIG. 7. The zero-time resistance was 320 ohms without the neutralizing capacitors (see FIG. 6), and the resistance in the same solution was 225 ohms after the neutralizing capacitors were added (see FIG. 7).

The equipment used to measure blood resistivity ($\rho$) and its transient change following an injection of the indicator is fully described in a previous patent to Geddes, et al., U.S. Pat. No. 4,572,206, which is hereby incorporated by reference. A summary of the measurement technique disclosed in the Geddes et al. patent will be provided for illustration purposes.

From $\rho$, the resistivity of the blood, it is possible to obtain the calibration factor $\Delta\rho/\Delta C$, the manner in which blood changes its resistivity ($\Delta\rho$) with a change in sodium chloride concentration ($\Delta C$): $\Delta\rho/\Delta C = B\rho^\beta$, where B and $\beta$ are species-dependent quantities. Blood resistance (R) is what is measured with the catheter conductivity cell; blood resistivity $\rho = R/K$, where k is the conductivity cell constant which is determined at the time of manufacture of the catheter.

A calibrating resistor $R_K$, as shown in FIG. 1, is incorporated into the connector that joins the catheter to the measuring apparatus. $R_K$ provides the measuring instruments with the information necessary to process the dilution curve from ohms to concentration change and thereby calculate the cardiac output indicator dilution curve accurately. FIG. 1B presents a typical calculation of cardiac output (CO) from a dilution curve recorded following the injection of 2 ml. of 5% saline into the right atrium with a catheter-tip conductivity cell located in the pulmonary artery of a subject.

Figure 5:
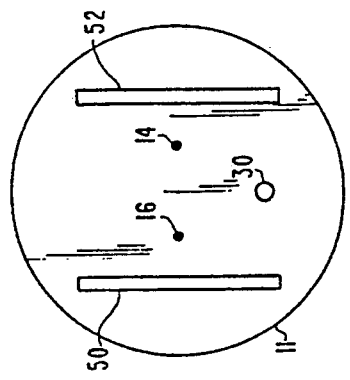
FIG. 5 is an end view of a catheter according to the present invention illustrating another arrangement for the electrodes located at the distal end of the catheter of FIG. 1.

Referring now to FIG. 5, another arrangement for the electrodes located at the distal end of catheter 11 is shown. Electrodes 50 and 52 connected to the conductors 12 and 18 are constructed by crimping a piece of stainless steel tubing to the ends of the conductors 12 and 18. A tight crimp, producing a continuous metal surface across each electrode face, yields good results. Alternative techniques for attaching the electrode to one of the catheter conductors, including brazing, silver soldering or resistive welding, are also contemplated. Electrodes 50 and 52 are crimped onto conductors 12 and 18, the current injection conductors, to provide a larger surface area contact for the electrode-electrolyte interface. Preferably, the electrodes 50 and 52 are constructed of silver, gold, platinum or stainless steel, or any other conductive material which is not subject to rapid corrosion while in contact with venous or bodily fluids. The potential-sensing electrodes 14 and 16 need not have as large a surface area contact with the electrolyte because the current flowing through those conductors is minuscule by comparison to that flowing between electrodes 50 and 52 and the surrounding electrolyte. Further, use of very high input impedance instrumentation amplifiers or FET input op amps having electrodes 16 and 14 connected to an input of the amplifier further reduces the requirements for large surface area contact between electrodes 14 and 16 and the venous solution. Port 30 is an optional pressure measurement port for measuring venous pressure at the distal end of catheter body 11.

Referring now to FIG. 8, an alternative arrangement for connecting the catheter 10 of FIG. 1 to measurement equipment is shown. Again, current source 19 supplies a constant alternating current signal to conductors 12 and 18 of catheter 10. Conductors 14 and 16 are connected to differential inputs of amplifier 23, a high input impedance amplifier. Capacitors C1 and C2 are shown as part of the measurement equipment in this figure, in contrast with FIG. 1 wherein capacitor C1 and C2 are incorporated into the body of the catheter 11. Resistor $R_K$ is connected at one lead to a reference voltage $V_{ref}$ and at a second lead to a precision resistor $R_p$ and to computer 60. By supplying a reference voltage signal to resistor $R_K$ via resistor $R_p$ and knowing the value of the precision resistor $R_p$, the computer can, via an analog input or A/D converter, determine the voltage drop across resistor $R_K$. The resistance $R_K$ is determined using basic electrical formulas, together with the voltage $V_{ref}$, the resistance $R_p$, and the voltage present at the junction of resistors $R_K$ and $R_p$. At another analog input, computer 60 is connected with the output of amplifier 23. Computer 60 calculates new values for the blood resistivity taking into account the value of resistor $R_K$ and supplies an output signal to display 62 and recorder 64 for permanent recording of the blood resistivity information.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. An indicator-dilution method for measuring cardiac output, said method comprising the steps of:
   placing a conductivity cell in a flow path of blood;
   compensating stray and distributed capacitances of said conductivity cell;
   electrically calibrating said conductivity cell without withdrawing blood from said flow path, said calibrating being accomplished by utilizing said conductivity cell to generate an output signal indicative of baseline blood resistivity;
   injecting an indicator into said blood flow path and obtaining an output signal from said conductivity cell indicative of blood resistivity as altered by said indicator; and
   determining cardiac output from said output signal indicative of baseline blood resistivity and said output signal indicative of altered blood resistivity which is a dilution curve.

2. The method of claim 1 wherein said conductivity cell includes a plurality of electrodes extending outward from said conductivity cell, each of said electrodes connected to a respective electrode wire, each of said electrodes formed so that the surface area of said electrode exposed to blood flow is larger than the cross-sectional area of said electrode wires.

3. The method of claim 2 wherein said electrodes are formed so that each of said electrodes is adapted to be situated perpendicular to the direction of blood flow.

4. The method of claim 1 including electrical determination of the conductivity cell constant of said conductivity cell after said conductivity cell is placed in the flow path of blood.

5. The method of claim 4 wherein an identifier device is attached to said conductivity cell, said identifier device having a detectable, measurable electronic parameter indicative of said conductivity cell constant.

6. The method of claim 5 wherein said identifier device is a resistor.

7. A method for measuring cardiac output with a conductivity cell catheter, said catheter having a proximal end and a distal end, said method comprising the steps of:
- positioning a detector on said distal end of said catheter;
- providing electrical leads extending through said catheter from said detector to said proximal end of said catheter;
- neutralizing stray capacitance associated with said electrical leads;
- inserting said catheter into a body such that said detector is in a flow path of blood in said body;
- electrically calibrating said detector without withdrawing blood from said body, said calibrating including electrically exciting said detector so that said detector provides an output signal indicative of baseline blood resistivity;
- injecting an indicator into said blood flow path and electrically exciting said detector so that said detector provides an output signal indicative of blood resistivity as altered by said indicator; and
- determining cardiac output from said output signal indicative of baseline blood resistivity and said output signal indicative of altered blood resistivity.

8. The method of claim 7 wherein said detector is a tetrapolar conductivity cell, and wherein said method includes electrically exciting a first pair of electrodes of said tetrapolar conductivity cell to develop a potential indicative of baseline blood resistivity on a second pair of electrodes of said tetrapolar conductivity cell.

9. The method of claim 8 wherein said electrodes extend out from the tip of the distal end of said catheter, said electrodes adapted to be situated approximately in a line normal to the direction of blood flow.

10. The method of claim 8 including electrically identifying a conductivity cell constant specific to said tetrapolar conductivity cell after said catheter is inserted into said body by measuring an electrical parameter of an electrical identifier located within said catheter and having leads extending out of the proximal end of said catheter.

11. The method of claim 10 wherein said electrical component is a resistor and said measurable electrical characteristic is resistance.

12. The method of claim 7 wherein said providing step includes providing electrical leads each having a substantially uniform cross-sectional area, and wherein said positioning step includes providing on said distal end a pair of electrodes each connected to one of said leads and each having an exposed surface area substantially larger than the cross-sectional area of the lead to which it is connected.

13. The method of claim 12 wherein said electrodes extend out from the tip of the distal end of said catheter and said electrodes are positioned approximately perpendicular to the direction of blood flow.

14. An apparatus for enabling measurement of cardiac output by determination of blood resistivity, said apparatus comprising:
- a conductivity cell having a plurality of electrodes;
- capacitance compensation means connected to said conductivity cell for neutralizing stray and distributed capacitances;
- positioning means for positioning said conductivity cell in the flow path of blood;
- wherein said positioning means includes a catheter having said conductivity cell attached to the distal end of said catheter and means for preventing said electrodes from contacting a wall defining the flow path of blood, and wherein said conductivity cell is a tetrapolar conductivity cell having four electrodes, said catheter also including four conductors extending along and within the entire length of said catheter, said four conductors each connected to one of said four electrodes; and
- wherein said electrodes emerge in a line from the cross-section of the distal end of said catheter, and the outer pair of said electrodes having exposed surfaces substantially larger than the cross-sectional area of said conductors.

15. The catheter of claim 14 wherein said electrodes are positioned in a line across the distal end of said catheter normal to the direction of blood flow.

16. The catheter of claim 14 including an indicator injection lumen and an indicator injection port, said indicator injection lumen communicating with said indicator injection port, said indicator injection port located near the distal end of said catheter.

17. The catheter of claim 16 wherein said catheter includes means for preventing said electrodes from contacting a wall defining the flow path of blood and situated so that said means for preventing electrodes from contacting a wall is between said indicator injection port and said distal end of said catheter.

18. The catheter of claim 17 including a second lumen, and wherein said means for preventing said electrodes from contacting a wall is a balloon communicating with said second lumen.

19. The catheter of claim 18 wherein said catheter includes a third lumen communicating with a port located between said balloon and said distal end of said catheter.

20. An apparatus for enabling measurement of cardiac output by determination of blood resistivity, said apparatus comprising:
- a catheter having a proximal and a distal end and adapted for insertion into a body so that the distal end of said catheter is in the flow path of blood in said body, said catheter having four conductors symmetrically contained within the body of said catheter;
- a tetrapolar conductivity cell attached to said catheter, said conductivity cell having four electrodes arranged substantially in a line and connected to said four conductors, forming an inner pair and outer pair of electrodes, said outer pair of said electrodes having an exposed surface area larger than the cross-sectional area of each of said conductors, said electrodes extending out of said distal end of said catheter, and said electrodes positioned substantially perpendicular to the direction of blood flow;

a constant-current source connected with the outer pair of said electrodes of said conductivity cell;

isolation amplifying means connected with said conductors connected to the inner pair of said electrodes for amplifying a potential appearing on the inner pair of said electrodes and providing an isolated analog output of blood resistivity for enabling inscribing of curve corresponding to blood resistivity;

a first capacitor connected between one of said outer electrodes and one of said inner electrodes, and a second capacitor connected between the remainder of said electrodes, said first and second capacitors located at the proximal end of said catheter and electrically connected to said electrodes via said conductors;

electrical identification means for identifying the conductivity cell constant peculiar to said catheter and conductivity cell in combination, said identification means having an electrical connection at the proximal end of said catheter; and indicating means connected with said first amplifying means for indicating resistivity.

21. The apparatus of claim 20 wherein said outer electrodes are metal tubes crimped to said conductors and contained within the distal end of said catheter, said crimped tubes being exposed at the distal end of said catheter.

22. The apparatus of claim 21 wherein epoxy is applied to said electrodes at the distal end of said catheter to fix said electrodes in position relative to one another.

23. The apparatus of claim 20 wherein said first and second capacitors are contained within said catheter and said catheter includes a connector attached to said proximal end for connecting said four conductors to said constant-current source and said isolation amplifying means.

* * * * *

UNITED STATES PATENT AND TRADEMARK OFFICE
CERTIFICATE OF CORRECTION

PATENT NO. : 5,092,339
DATED : March 3, 1992
INVENTOR(S) : Leslie A. Geddes et al.

It is certified that error appears in the above-identified patent and that said Letters Patent is hereby corrected as shown below:

In item [76] of the title page, please change "Anthony C. Raghep" to --Anthony O. Ragheb--.
In item [54] of the title page, Abstract, line 11, please change "cather/-" to --catheter/---.

Signed and Sealed this

Twelfth Day of October, 1993

Attest:

BRUCE LEHMAN

Attesting Officer

Commissioner of Patents and Trademarks